US012327349B2

(12) United States Patent
Vaidya et al.

(10) Patent No.: US 12,327,349 B2
(45) Date of Patent: Jun. 10, 2025

(54) FULLY AUTOMATED ASSESSMENT OF CORONARY VULNERABLE PLAQUE IN CORONARY CT IMAGES USING RADIOMIC FEATURES

(71) Applicant: SIEMENS HEALTHINEERS AG, Forchheim (DE)

(72) Inventors: Pranjal Vaidya, Mayfield Heights, OH (US); Mehmet Akif Gulsun, Princeton, NJ (US); Puneet Sharma, Princeton Junction, NJ (US)

(73) Assignee: Siemens Healthineers AG, Forchheim (DE)

( * ) Notice: Subject to any disclaimer, the term of this patent is extended or adjusted under 35 U.S.C. 154(b) by 382 days.

(21) Appl. No.: 17/648,974

(22) Filed: Jan. 26, 2022

(65) Prior Publication Data

US 2023/0071558 A1 Mar. 9, 2023

Related U.S. Application Data

(60) Provisional application No. 63/260,518, filed on Aug. 24, 2021.

(51) Int. Cl.
*G06V 10/25* (2022.01)
*G06T 7/00* (2017.01)
(Continued)

(52) U.S. Cl.
CPC ............ *G06T 7/0012* (2013.01); *G06V 10/25* (2022.01); *G06V 10/44* (2022.01); *G06V 10/764* (2022.01);
(Continued)

(58) Field of Classification Search
CPC ......... G06T 7/0012; G06T 2207/10081; G06T 2207/30096; G06T 2207/30101;
(Continued)

(56) References Cited

U.S. PATENT DOCUMENTS

| 2010/0067760 A1* | 3/2010 | Zhang | G06T 7/143 |
| | | | 382/130 |
| 2011/0224542 A1* | 9/2011 | Mittal | G06T 7/0016 |
| | | | 600/425 |

(Continued)

OTHER PUBLICATIONS

European Patent Application No. 21171600.6, filed Apr. 30, 2021 entitled "Computer-Implemented Method and Evaluation System for Evaluating at least One Image Data Set of an Imaging Region of a Patient, Computer Program and Electronically Readable Storage Medium, " 65 pgs.

(Continued)

*Primary Examiner* — Syed Haider

(57) ABSTRACT

Systems and methods for automatic assessment of a lesion are provided. One or more input medical images of a vessel of a patient is received. A lesion is defined in the one or more input medical images. A region of interest around the lesion is defined in the one or more input medical images. Radiomic features are extracted from the region of interest.

(Continued)

An assessment of the lesion is determined using a machine learning based classifier network based on the radiomic features. The assessment of the lesion is output.

25 Claims, 6 Drawing Sheets

(51) Int. Cl.
 *G06V 10/44* (2022.01)
 *G06V 10/764* (2022.01)
 *G06V 10/82* (2022.01)
(52) U.S. Cl.
 CPC .... *G06V 10/82* (2022.01); *G06T 2207/10081* (2013.01); *G06T 2207/30096* (2013.01); *G06T 2207/30101* (2013.01); *G06V 2201/032* (2022.01)
(58) Field of Classification Search
 CPC ........ G06V 10/25; G06V 10/82; G06V 10/44; G06V 10/764; G06V 2201/032
 See application file for complete search history.

(56) References Cited

U.S. PATENT DOCUMENTS

| | | | | |
|---|---|---|---|---|
| 2012/0243764 | A1* | 9/2012 | Dey | A61B 6/032 |
| | | | | 600/425 |
| 2016/0235373 | A1* | 8/2016 | Sharma | G16H 10/40 |
| 2018/0276498 | A1* | 9/2018 | Madabhushi | A61B 5/4842 |
| 2021/0073978 | A1* | 3/2021 | Schmitt | G16H 50/20 |
| 2021/0209757 | A1* | 7/2021 | Min | A61B 6/463 |
| 2021/0374951 | A1* | 12/2021 | Antoniades | A61B 6/501 |
| 2023/0255581 | A1* | 8/2023 | Jang | A61B 6/032 |
| | | | | 382/128 |

OTHER PUBLICATIONS

Gillies et al., "Radiomics: Images Are More than Pictures, They Are Data," 2016, Radiology, vol. 278, No. 2, pp. 563-577.
Kolossváry et al., "Radiomic Features Are Superior to Conventional Quantitative Computed Tomographic Metrics to Identify Coronary Plaques With Napkin-Ring Sign," 2017, Circulation: Cardiovascular Imaging, vol. 10, No. 12, 9 pgs.
Van Griethuysen et al., "Computational Radiomics System to Decode the Radiographic Phenotype," 2017, Cancer Research vol. 77, Focus on Computer Resources, pp. e104-e107.
Extended European Search Report (EESR) mailed Jan. 16, 2023 in corresponding European Patent Application No. 22191499.7.
Oikonomou, et al.; "A novel machine learning-derived radiotranscriptomic signature of perivascular fat improves cardiac risk prediction using coronary CT angiography", European Heart Journal, vol. 40, No. 43, Nov. 14, 2019, pp. 3529-3543.
Oikonomou, et al.; "Online Supplemental Material: A novel machine learning-derived radiotranscriptomic signature of perivascular fat improves cardiac risk prediction using coronary CT angiography", European Heart Journal, vol. 40, No. 43; Sep. 3, 2019; pp. 1-34.
Lin, et al.; "Myocardial Infarction 1-15 Associates With a Distinct Pericoronary Adipose Tissue Radiomic Phenotype A Prospective Case-Control Study", JACC: Cardiovascular Imaging, Elsevier, Amsterdam, NL, vol. 13, No. 11; Aug. 26, 2020, pp. 2371-2383.
Kolossvary, et al.; "Advanced atherosclerosis imaging by CT: Radiomics, machine learning and deep learning", Journal of Cardiovascular Computed Tomography, Elsevier, Amsterdam, NL, vol. 13, No. 5, Apr. 21, 2019, pp. 274-280.
Zhang; et al: "Identification of high-risk carotid plaque with MRI-based radiomics and machine learning", European Radiology, Springer Berlin Heidelberg, Berlin/Heidelberg, vol. 31, No. 5; Oct. 17, 2020, pp. 3116-3126.

* cited by examiner

\# FULLY AUTOMATED ASSESSMENT OF CORONARY VULNERABLE PLAQUE IN CORONARY CT IMAGES USING RADIOMIC FEATURES

This application claims the benefit of U.S. Provisional Application No. 63/260,518, filed Aug. 24, 2021, the disclosure of which is herein incorporated by reference in its entirety.

TECHNICAL FIELD

The present invention relates generally to assessment of coronary vulnerable plaque in coronary CT (computed tomography) images, and in particular to fully automated assessment of coronary vulnerable plaque in coronary CT images using radiomic features.

BACKGROUND

Coronary artery disease involves the reduction of blood flow to the heart due to the buildup of plaque in the coronary arteries. Vulnerable plaque is plaque that is at a high risk for rupturing, resulting in a heart attack, stroke, or other heart issues. In the current clinical practice, vulnerable plaque is detected by manual inspection and observation of CT (computed tomography) images by radiologists. However, the manual detection of vulnerable plaque is subjective, labor intensive, and requires specialized training and experience.

BRIEF SUMMARY OF THE INVENTION

In accordance with one or more embodiments, systems and methods for automatic assessment of a lesion are provided. One or more input medical images of a vessel of a patient is received. A lesion in the one or more input medical images is defined. A region of interest around the lesion is defined in the one or more input medical image. Radiomic features are extracted from the region of interest. An assessment of the lesion is determined using a machine learning based classifier network based on the radiomic features. The assessment of the lesion is output.

In one embodiment, the input medical image is a computed tomography image of coronary plaque. The assessment of the lesion is determined by classifying the lesion as being vulnerable plaque or non-vulnerable plaque. The assessment of the lesion may be determined as a probability score indicating a degree of vulnerability of the lesion. The assessment of the lesion may be determined as a classification of a type of vulnerable plaque of the lesion.

In one embodiment, the region of interest is automatically defined based on at least one of a segmentation of an outer wall of a coronary artery or a segmentation of coronary lumen. The region of interest may be automatically defined as a segmentation mask of the outer wall of the coronary artery. The region of interest may be automatically defined as a segmentation mask of the outer wall of a coronary artery excluding the coronary lumen. The region of interest may be automatically defined as a segmentation mask surrounding the outer wall of the coronary artery.

In one embodiment, the radiomic features comprise one or more of first order statistical features, second order statistical features, or higher order statistical features. In another embodiment, the radiomic features comprises one or more of size and shape based features, descriptors of an image intensity histogram of the input medical image, descriptors of relationships between image voxels, texture features, or fractal features. The radiomic features may be extracted by selecting a best set of the radiomic features for determining the assessment of the lesion.

In one embodiment, an additional input medical image of the lesion is received. The additional input medical image is acquired at a different time point than the input medical image. The defining, the extracting, and the determining are repeated using the additional input medical image as the input medical image to determine an additional assessment of the lesion. Changes in the assessment of the lesion and the additional assessment of the lesion are presented.

These and other advantages of the invention will be apparent to those of ordinary skill in the art by reference to the following detailed description and the accompanying drawings.

DETAILED DESCRIPTION

The present invention generally relates to methods and systems for fully automated assessment of coronary vulnerable plaque in coronary CT (computed tomography) images using radiomic features. Embodiments of the present invention are described herein to give a visual understanding of such methods and systems. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, it is to be understood that embodiments of the present invention may be performed within a computer system using data stored within the computer system.

Embodiments described herein provide for the fully automated assessment of coronary vulnerable plaque in coronary CT images. Radiomic features extracted inside a region of interest around coronary lesions in an input medical image are used to differential vulnerable (or high-risk) plaque from non-vulnerable plaque in coronary arteries. Advantageously, by using radiomic features, embodiments described herein provide for the fully automated assessment of vulnerable plaque with high accuracy without requiring user input.

Figure 1:
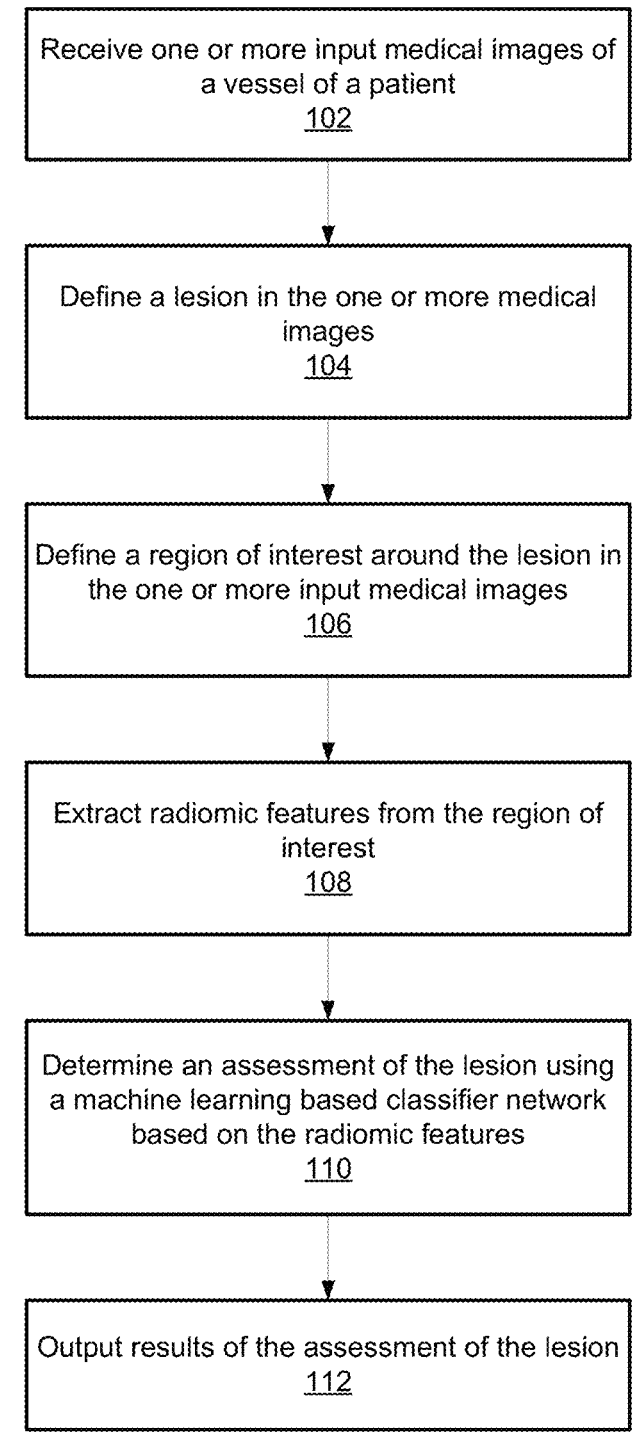
FIG. 1 shows a method for automatically assessing a lesion based on radiomic features, in accordance with one or more embodiments.

FIG. 1 shows a method 100 for automatically assessing a lesion based on radiomic features, in accordance with one or more embodiments. The steps of method 100 may be performed by one or more suitable computing devices, such as, e.g., computer 602 of FIG. 6.

At step 102 of FIG. 1, one or more input medical images of a vessel of a patient are received. In one embodiment, the input medical images are CT images (or scans). However, the input medical images may comprise any other suitable modality, such as, e.g., MRI (magnetic resonance imaging), ultrasound, x-ray, or any other medical imaging modality or combinations of medical imaging modalities. The input medical images may be a 2D (two dimensional) image or a 3D (three dimensional) volume, and may comprise a single image or a plurality images. The input medical images may be received directly from an image acquisition device, such as, e.g., a CT scanner, as the images are acquired, or can be received by loading previously acquired images from a storage or memory of a computer system or receiving images that have been transmitted from a remote computer system.

At step 104 of FIG. 1, a lesion in the one or more input medical images is defined. In one embodiment, the lesion may be automatically defined (e.g., using a machine learning based lesion detection network). The lesion may also be manually identified by a user. In one embodiment, the lesion comprises coronary plaque depicted in an input medical image of coronary arteries of a patient. However, the lesion may be a tumor, a nodule, an ulcer, or any other abnormality of the patient.

At step 106 of FIG. 1, a region of interest around the lesion is defined in the one or more input medical images. In one embodiment, the region of interest is automatically defined using one or more machine learning based segmentation networks. For example, the region of interest may be automatically defined based on a segmentation of the outer wall of the coronary artery and/or the coronary lumen. The region of interest may be defined as, e.g., a segmentation mask of the outer wall of the coronary artery, a segmentation mask of the outer wall of the coronary artery excluding the lumen, or a segmentation mask surrounding the outer wall of the coronary artery. The segmentation mask may partially comprise background. In another embodiment, the region of interest is defined manually by a user.

Figure 2:
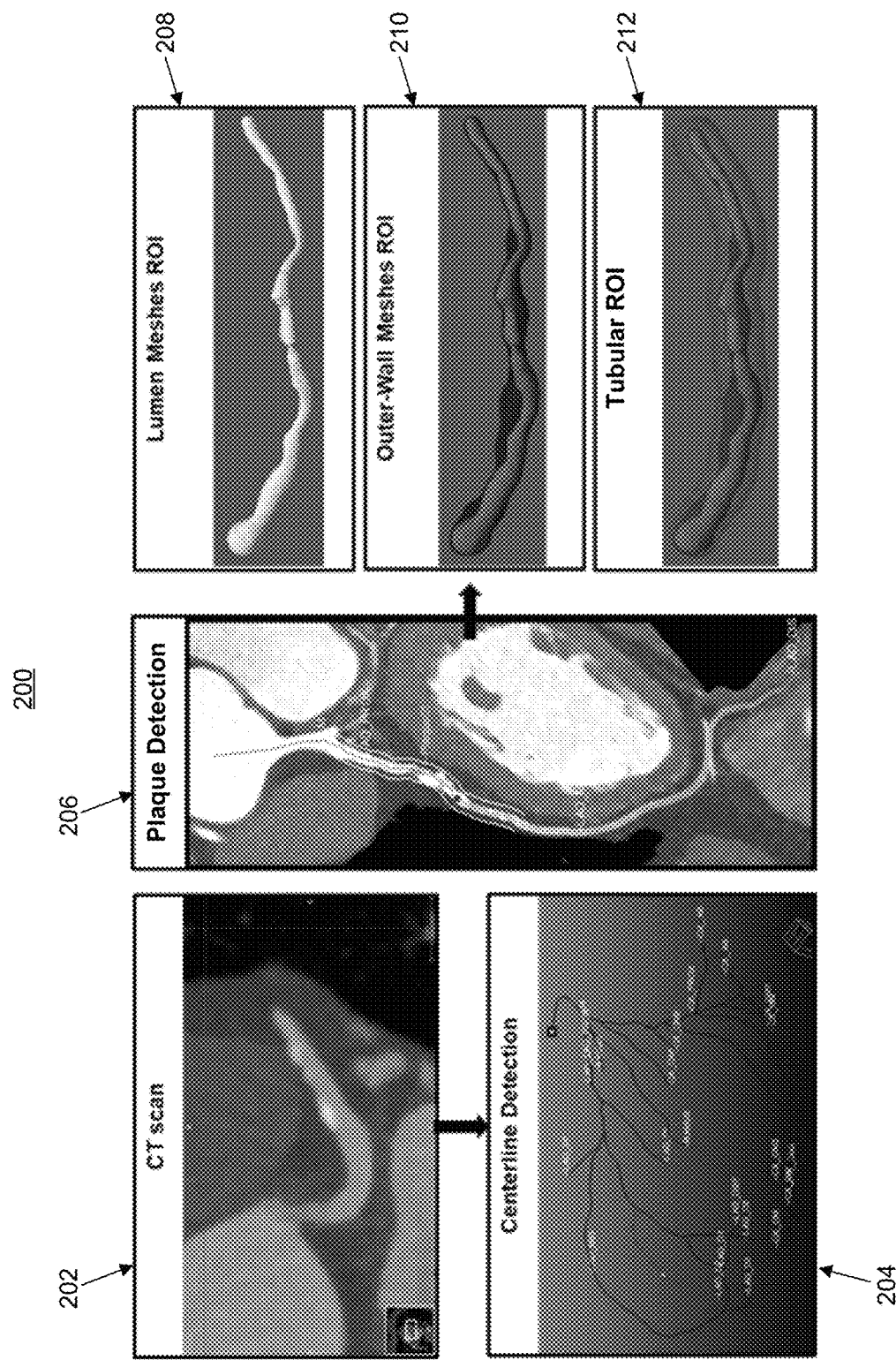
FIG. 2 shows a workflow for automatically defining a region of interest around plaque in an input medical image, in accordance with one or more embodiments.

FIG. 2 shows a workflow 200 for automatically defining a region of interest around plaque in an input medical image, in accordance with one or more embodiments. At step 202, a CT scan of coronary arteries of a patient is received. The CT scan depicts plaque in the coronary arteries. At step 204, centerline detection is performed to detect the centerlines of the coronary arteries. Centerline detection may be manually performed or automatically performed using a machine learning based centerline detection network or any other suitable approach. At step 206, plaque detection is performed to localize the start and end markers of plaque from the CT scan along the detected centerlines of the coronary arteries. Plaque detection may be performed using a machine learning based plaque detection network. Based on a coronary section defined between detected plaque markers, one or more of ROIs (region of interest) are determined based on lumen segmentation, outer wall segmentation, plaque segmentation (lumen removed from outer wall segmentation) or tubular segmentation surrounding outer wall at steps 208, 210, and 212 as the region of interest around the plaque.

At step 108 of FIG. 1, radiomic features are extracted from the region of interest. Radiomic features are features of a radiographic image that are not apparent or obvious to the human eye. In one embodiment, the radiomic features may comprise first-order statistical feature families (features based on first order statistics such as, e.g., based on individual voxels without spatial relationship) or features based on second or higher order statistical features (such as, e.g., textural features based on inter-relationship between voxels). In other embodiments, the radiomic features may comprise, for example, size and shape based—features (e.g., elongation, least axis length, maximum 2D diameter row, maximum 2D diameter slice, minor axis length, sphericity, etc.), descriptors of the image intensity histogram, descriptors of the relationships between image voxels (e.g., gray-level co-occurrence matrix (GLCM), gray level run length matrix (GLRLM), gray-level size zone matrix (GLSZM), gray level dependence matrix (GLDM), and neighborhood gray tone difference matrix (NGTDM) derived textures), texture features extracted from filtered images, and fractal features. The radiomic features may be extracted using any suitable technique. In one embodiment, the best set of radiomic features are selected for determining an assessment of the lesion using the mRMR (minimum redundancy maximum relevance) feature selection algorithm.

At step 110 of FIG. 1, an assessment of the lesion is determined using a machine learning based classifier network based on the radiomic features. The classifier network receives as input the radiomic features and generates as output the assessment of the lesion. In one embodiment, the assessment of the lesion is a classification of the lesion as being vulnerable (or high risk) plaque or non-vulnerable plaque. For example, the classification may be represented as a probability score indicating a probability that the plaque is vulnerable (or non-vulnerable) or indicating a degree of vulnerability. In another embodiment, the assessment of the lesion is a classification of a type of vulnerable plaque of the lesion, such as, e.g., napkin ring sign, low attenuation, spotty calcification, positive remodeling, etc. However, the assessment of the lesion may comprise any other suitable assessment. The classifier may be implemented according to any suitable architecture, such as, e.g., logistic regression, LDA (linear discriminant analysis), QDA (quadratic discriminant analysis), SVM (support vector machine), and RF (random forest).

The classifier network is trained during a prior offline or training stage using a set of training data. The training data is annotated with ground truths to identify the classification. The ground truth annotations may be based on clinical interpretation of medical images or follow-up data where certain plaque rupture events are used to identify specific positive examples. Once trained, the classifier network may be applied during an online or testing stage (e.g., at step 110 of FIG. 1).

At step 112, results of the assessment of the lesion are output. For example, the results of the assessment of the lesion can be output by displaying the results of the assessment of the lesion on a display device of a computer system, storing the results of the assessment of the lesion on a memory or storage of a computer system, or by transmitting the results of the assessment of the lesion of the assessment to a remote computer system.

In one embodiment, the results of the assessment of the lesion are output to various coronary analysis systems or applications. For example, the results of the assessment of the lesion may be output to a system for modifying CAD-RADS (coronary artery disease reporting and data system) data for automated reporting. In another example, the results of the assessment of the lesion may be output to a system for coronary plaque quantification. In a further example, the results of the assessment of the lesion may be output to a system for treatment planning and optimization for device-based treatment (e.g., stenting or percutaneous coronary intervention, balloon angioplasty, atherectomy, etc.), as well as drug-based treatment.

In one embodiment, the steps of method 100 of FIG. 1 may be repeatedly performed on one or more additional input medical images of the lesion to determine one or more additional assessments of the lesions. The input medical image and the one or more additional input medical images are each acquired at different time points. Accordingly, changes in the assessment of the lesion and the one or more additional assessments of the lesions over time may be presented (e.g., to characterize changes in plaque vulnerability). For example, the classifier network (at step 108) may generate a probability score indicating the degree of vulnerability of the plaque at each time point. The change in plaque vulnerability over time may be output (e.g., presented) for optimizing medical treatment of the patient, such as, e.g., drug dose.

Figure 3:
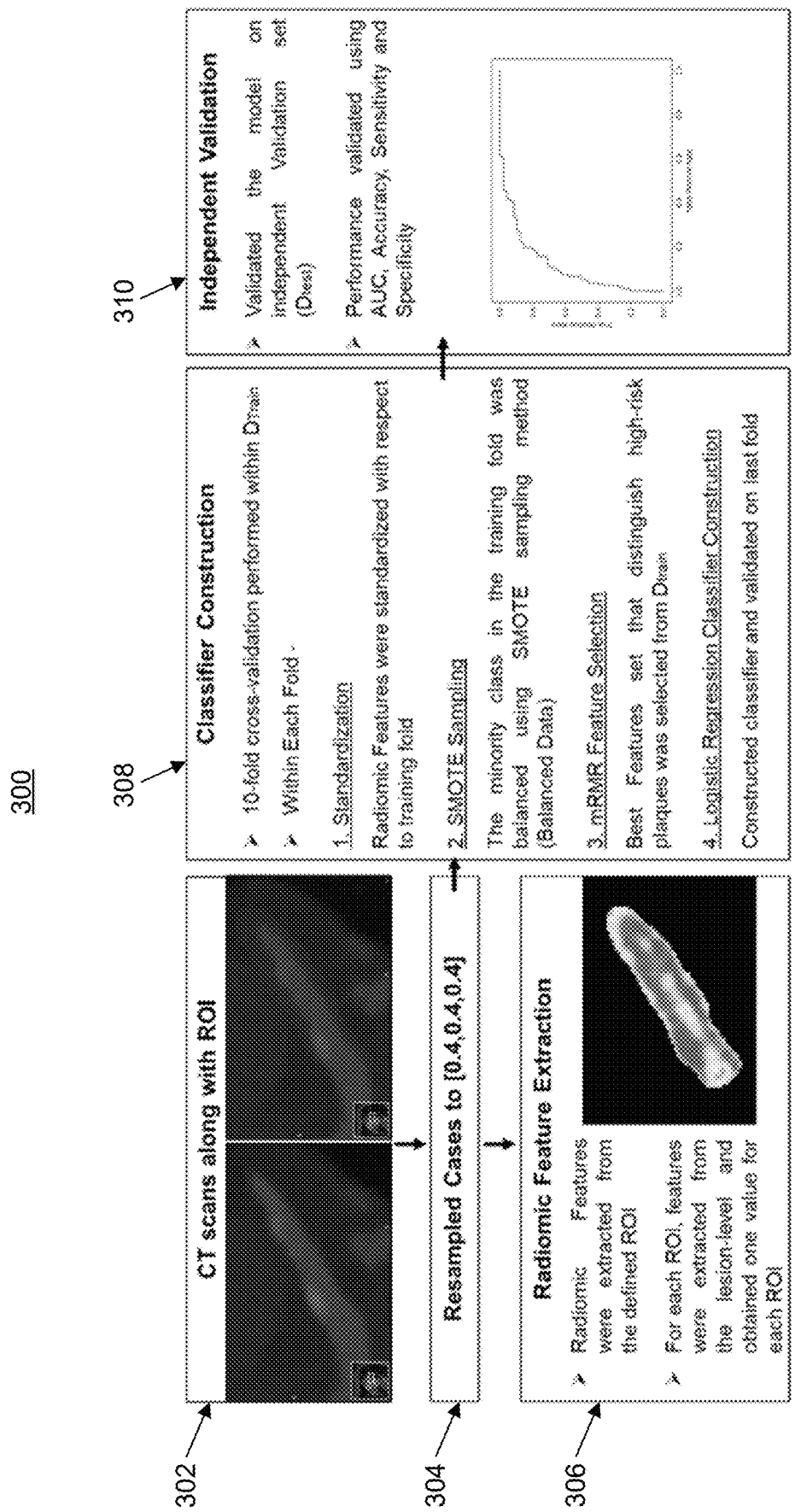
FIG. 3 shows a workflow for validating embodiments described herein.

FIG. 3 shows a workflow 300 for experimentally validating one or more embodiments described. Embodiments described herein utilized radiomic features for differentiating vulnerable plaque from non-vulnerable plaque in CT images. The radiomic features capture textural patterns of a defined region of interest from radiographic scans that are not apparent or obvious to the human eye.

In workflow 300, a dataset comprising CT scans with ROIs annotated therein is received at step 302. The ROIs were defined around plaques to extract radiomic features. ROIs around the plaques included a coronary artery segment with the plaque built up that included lumen, its surrounding outer wall, and a 2 mm band around the outer wall. At step 304, the CT scans were resampled to the standard size of, e.g., [0.4, 0.4, 0.4].

At step 306, 2D radiomic features were extracted from the defined regions of interest at a lesion level. Radiomic features were extracted from each ROI from the lesion-level. The radiomic features included shape-based feature families, first-order feature families and higher-order feature families were extracted from all the given ROIs. The higher order radiomic features included features from GLCM, GLRLM, GLSZM, NGTDM, and GLDM feature families. First-order statistical feature families include features based on first order statistics such as, e.g., based on individual voxels without spatial relationship. Higher-order family includes features based on second or higher order statistical features such as, e.g., textural features based on interrelationship between voxels.

After extracting the radiomic features, a classifier was constructed at step 308. $D_{Train}$ was used for constructing the classifier and for selecting the best features. Within $D_{Train}$, 10-fold cross-validation was performed. For each fold, four steps were performed: standardization, sampling, feature selection, and classifier construction. First, all features were standardized with respect to the training fold. Second, SMOTE (synthetic minority oversampling technique) sampling method was performed to oversample the minority class and balance the dataset within the training fold. Third, the best feature set was selected using the training fold with the mRMR feature selection algorithm. Fourth, final regression classifier construction was performed to construct the classifier and validate the classifier on the last fold.

The performance of the best feature set was validated on the remaining test cases using the classifier at step 410. The classifier performance was evaluated based on the ROC-AUC (area under receiver operating characteristic curve), accuracy, sensitivity, and specificity. Multiple classifiers, including, for example, logistic regression, LDA, QDA, SVM, and RF were tested for performance. The best feature set was evaluated using box-and-whisker plots and the statistical significance between the two groups was evaluated using the Wilcoxon rank-sum text along with two-sided p-values. The best features were obtained from shape-based feature families followed by first order features and features from GLCM, NGTDM and GLRLM feature families. The most predictive features are described in Table.

TABLE 1

| | Feature Family | Description |
|---|---|---|
| 1 | Grey Level Co-occurrence Matrix (GLCM) | Idmn |
| 2 | Grey Level Run Length Matrix (GLRLM) | Short Run Low Gray Level Emphasis |
| 3 | Neighborhood Grey Tone Difference Matrix (NGTDM) | Strength |
| 4 | First Order | Entropy |
| 5 | Shape | Elongation |
| 6 | Shape | Least Axis Length |
| 7 | Shape | Maximum 2D Diameter Row |
| 8 | Shape | Maximum 2D Diameter Slice |
| 9 | Shape | Minor Axis Length |
| 10 | Shape | Sphericity |

Embodiments described herein are described with respect to the claimed systems as well as with respect to the claimed methods. Features, advantages or alternative embodiments herein can be assigned to the other claimed objects and vice versa. In other words, claims for the systems can be improved with features described or claimed in the context of the methods. In this case, the functional features of the method are embodied by objective units of the providing system.

Furthermore, certain embodiments described herein are described with respect to methods and systems utilizing trained machine learning based networks (or models), as well as with respect to methods and systems for training machine learning based networks. Features, advantages or alternative embodiments herein can be assigned to the other claimed objects and vice versa. In other words, claims for methods and systems for training a machine learning based network can be improved with features described or claimed in context of the methods and systems for utilizing a trained machine learning based network, and vice versa.

In particular, the trained machine learning based networks applied in embodiments described herein can be adapted by the methods and systems for training the machine learning based networks. Furthermore, the input data of the trained machine learning based network can comprise advantageous features and embodiments of the training input data, and vice versa. Furthermore, the output data of the trained machine learning based network can comprise advantageous features and embodiments of the output training data, and vice versa.

In general, a trained machine learning based network mimics cognitive functions that humans associate with other human minds. In particular, by training based on training data, the trained machine learning based network is able to adapt to new circumstances and to detect and extrapolate patterns.

In general, parameters of a machine learning based network can be adapted by means of training. In particular, supervised training, semi-supervised training, unsupervised training, reinforcement learning and/or active learning can be used. Furthermore, representation learning (an alternative term is "feature learning") can be used. In particular, the parameters of the trained machine learning based network can be adapted iteratively by several steps of training.

In particular, a trained machine learning based network can comprise a neural network, a support vector machine, a decision tree, and/or a Bayesian network, and/or the trained machine learning based network can be based on k-means clustering, Q-learning, genetic algorithms, and/or association rules. In particular, a neural network can be a deep neural network, a convolutional neural network, or a convolutional deep neural network. Furthermore, a neural network can be an adversarial network, a deep adversarial network and/or a generative adversarial network.

Figure 4:
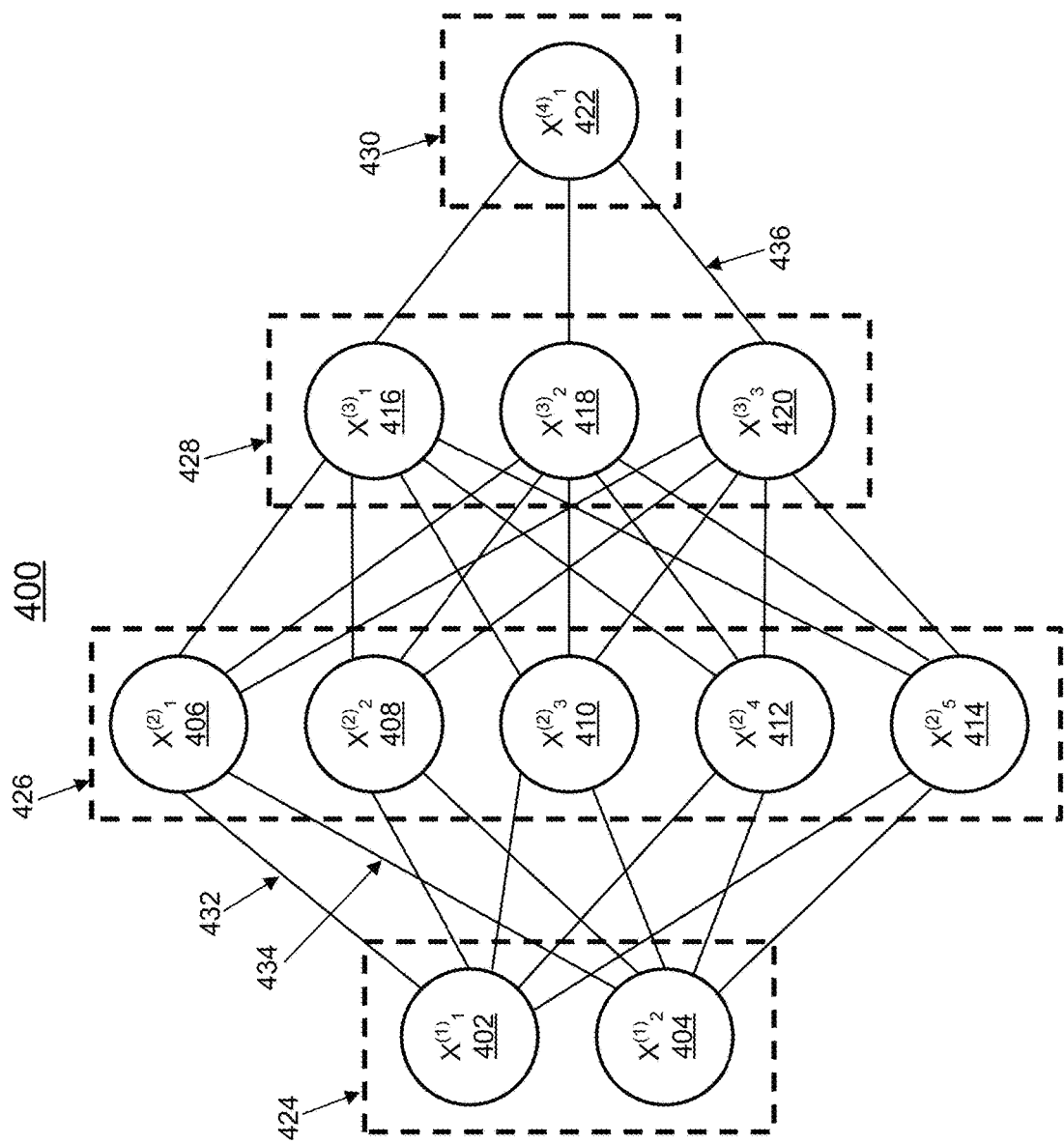
FIG. 4 shows an exemplary artificial neural network that may be used to implement one or more embodiments.

FIG. 4 shows an embodiment of an artificial neural network 400, in accordance with one or more embodiments. Alternative terms for "artificial neural network" are "neural network", "artificial neural net" or "neural net". Machine learning networks described herein, such as, e.g., the segmentation network utilized at step 104 and the classifier network utilized at step 108 of FIG. 1, the centerline detection network utilized at step 204 and the plaque segmentation network utilized at step 206 of FIG. 2, and the classifier utilized at step 208 of FIG. 3, may be implemented using artificial neural network 400.

The artificial neural network 400 comprises nodes 402-422 and edges 432, 434, ..., 436, wherein each edge 432, 434, ..., 436 is a directed connection from a first node 402-422 to a second node 402-422. In general, the first node 402-422 and the second node 402-422 are different nodes 402-422, it is also possible that the first node 402-422 and the second node 402-422 are identical. For example, in FIG. 4, the edge 432 is a directed connection from the node 402 to the node 406, and the edge 434 is a directed connection from the node 404 to the node 406. An edge 432, 434, ..., 436 from a first node 402-422 to a second node 402-422 is also denoted as "ingoing edge" for the second node 402-422 and as "outgoing edge" for the first node 402-422.

In this embodiment, the nodes 402-422 of the artificial neural network 400 can be arranged in layers 424-430, wherein the layers can comprise an intrinsic order introduced by the edges 432, 434, ..., 436 between the nodes 402-422. In particular, edges 432, 434, ..., 436 can exist only between neighboring layers of nodes. In the embodiment shown in FIG. 4, there is an input layer 424 comprising only nodes 402 and 404 without an incoming edge, an output layer 430 comprising only node 422 without outgoing edges, and hidden layers 426, 428 in-between the input layer 424 and the output layer 430. In general, the number of hidden layers 426, 428 can be chosen arbitrarily. The number of nodes 402 and 404 within the input layer 424 usually relates to the number of input values of the neural network 400, and the number of nodes 422 within the output layer 430 usually relates to the number of output values of the neural network 400.

In particular, a (real) number can be assigned as a value to every node 402-422 of the neural network 400. Here, $x^{(n)}_i$ denotes the value of the i-th node 402-422 of the n-th layer 424-430. The values of the nodes 402-422 of the input layer 424 are equivalent to the input values of the neural network 400, the value of the node 422 of the output layer 430 is equivalent to the output value of the neural network 400. Furthermore, each edge 432, 434, ..., 436 can comprise a weight being a real number, in particular, the weight is a real number within the interval $[-1, 1]$ or within the interval $[0, 1]$. Here, $w^{(m,n)}_{i,j}$ denotes the weight of the edge between the i-th node 402-422 of the m-th layer 424-430 and the j-th node 402-422 of the n-th layer 424-430. Furthermore, the abbreviation $w^{(n)}_{i,j}$ is defined for the weight $w^{(n,n+1)}_{i,j}$.

In particular, to calculate the output values of the neural network 400, the input values are propagated through the neural network. In particular, the values of the nodes 402-422 of the (n+1)-th layer 424-430 can be calculated based on the values of the nodes 402-422 of the n-th layer 424-430 by $$x_j^{(n+1)} = f(\Sigma_i x_i^{(n)} \cdot w_{i,j}^{(n)}).$$

Herein, the function f is a transfer function (another term is "activation function"). Known transfer functions are step functions, sigmoid function (e.g. the logistic function, the generalized logistic function, the hyperbolic tangent, the Arctangent function, the error function, the smoothstep function) or rectifier functions. The transfer function is mainly used for normalization purposes.

In particular, the values are propagated layer-wise through the neural network, wherein values of the input layer 424 are given by the input of the neural network 400, wherein values of the first hidden layer 426 can be calculated based on the values of the input layer 424 of the neural network, wherein values of the second hidden layer 428 can be calculated based in the values of the first hidden layer 426, etc.

In order to set the values $w^{(m,n)}_{i,j}$ for the edges, the neural network 400 has to be trained using training data. In particular, training data comprises training input data and training output data (denoted as $t_i$). For a training step, the neural network 400 is applied to the training input data to generate calculated output data. In particular, the training data and the calculated output data comprise a number of values, said number being equal with the number of nodes of the output layer.

In particular, a comparison between the calculated output data and the training data is used to recursively adapt the weights within the neural network 400 (backpropagation algorithm). In particular, the weights are changed according to $$w_{i,j}^{(n)} = w_{i,j}^{(n)} - \gamma \cdot \delta_j^{(n)} \cdot x_i^{(n)}$$

wherein $\gamma$ is a learning rate, and the numbers $\delta^{(n)}_j$ can be recursively calculated as $$\delta_j^{(n)} = (\Sigma_k \delta_k^{(n+1)} \cdot w_{j,k}^{(n+1)}) \cdot f'(\Sigma_i x_i^{(n)} \cdot w_{i,j}^{(n)})$$

based on $\delta^{(n+1)}_j$, if the (n+1)-th layer is not the output layer, and $$\delta_j^{(n)} = (x_k^{(n+1)} - t_j^{(n+1)}) \cdot f'(\Sigma_i x_i^{(n)} \cdot w_{i,j}^{(n)})$$

if the (n+1)-th layer is the output layer 430, wherein f' is the first derivative of the activation function, and $y^{(n+1)}_j$ is the comparison training value for the j-th node of the output layer 430.

Figure 5:
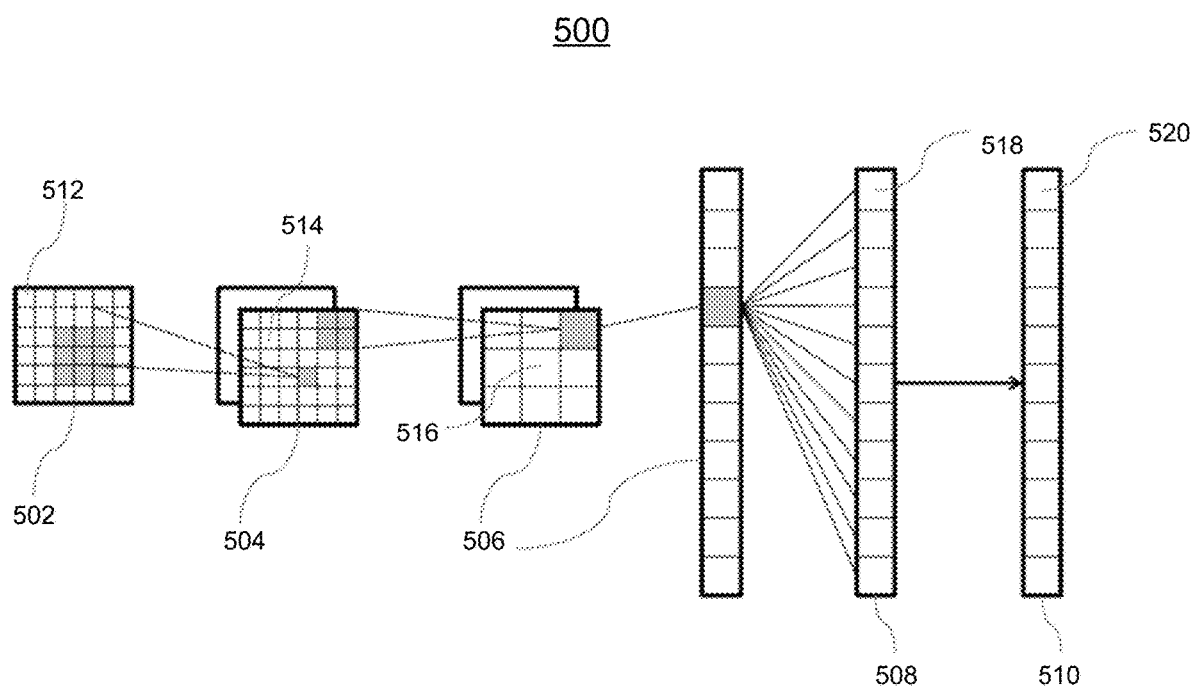
FIG. 5 shows a convolutional neural network that may be used to implement one or more embodiments.

FIG. 5 shows a convolutional neural network 500, in accordance with one or more embodiments. Machine learning networks described herein, such as, e.g., the segmentation network utilized at step 104 and the classifier network utilized at step 108 of FIG. 1, the centerline detection network utilized at step 204 and the plaque segmentation network utilized at step 206 of FIG. 2, and the classifier utilized at step 208 of FIG. 3, may be implemented using convolutional neural network 500.

In the embodiment shown in FIG. 5, the convolutional neural network comprises 500 an input layer 502, a convolutional layer 504, a pooling layer 506, a fully connected layer 508, and an output layer 510. Alternatively, the convolutional neural network 500 can comprise several convolutional layers 504, several pooling layers 506, and several fully connected layers 508, as well as other types of layers. The order of the layers can be chosen arbitrarily, usually fully connected layers 508 are used as the last layers before the output layer 510.

In particular, within a convolutional neural network 500, the nodes 512-520 of one layer 502-510 can be considered to be arranged as a d-dimensional matrix or as a d-dimensional image. In particular, in the two-dimensional case the value of the node 512-520 indexed with i and j in the n-th layer 502-510 can be denoted as $x^{(n)}_{[i,j]}$. However, the arrangement of the nodes 512-520 of one layer 502-510 does not have an effect on the calculations executed within the convolutional neural network 500 as such, since these are given solely by the structure and the weights of the edges.

In particular, a convolutional layer 504 is characterized by the structure and the weights of the incoming edges forming a convolution operation based on a certain number of kernels. In particular, the structure and the weights of the incoming edges are chosen such that the values $x^{(n)}_k$ of the nodes 514 of the convolutional layer 504 are calculated as a convolution $x^{(n)}_k = K_k * x^{(n-1)}$ based on the values $x^{(n-1)}$ of the nodes 512 of the preceding layer 502, where the convolution * is defined in the two-dimensional case as $$x_k^{(n)}[i,j] = (K_k * x^{(n-1)})[i,j] = \Sigma_i \Sigma_j K_k[i',j'] \cdot x^{(n-1)}[i-i',j-j'].$$

Here the k-th kernel $K_k$ is a d-dimensional matrix (in this embodiment a two-dimensional matrix), which is usually small compared to the number of nodes 512-518 (e.g. a 3×3 matrix, or a 5×5 matrix). In particular, this implies that the weights of the incoming edges are not independent, but chosen such that they produce said convolution equation. In particular, for a kernel being a 3×3 matrix, there are only 9 independent weights (each entry of the kernel matrix corresponding to one independent weight), irrespectively of the number of nodes 512-520 in the respective layer 502-510. In particular, for a convolutional layer 504, the number of nodes 514 in the convolutional layer is equivalent to the number of nodes 512 in the preceding layer 502 multiplied with the number of kernels.

If the nodes 512 of the preceding layer 502 are arranged as a d-dimensional matrix, using a plurality of kernels can be interpreted as adding a further dimension (denoted as "depth" dimension), so that the nodes 514 of the convolutional layer 504 are arranged as a (d+1)-dimensional matrix. If the nodes 512 of the preceding layer 502 are already arranged as a (d+1)-dimensional matrix comprising a depth dimension, using a plurality of kernels can be interpreted as expanding along the depth dimension, so that the nodes 514 of the convolutional layer 504 are arranged also as a (d+1)-dimensional matrix, wherein the size of the (d+1)-dimensional matrix with respect to the depth dimension is by a factor of the number of kernels larger than in the preceding layer 502.

The advantage of using convolutional layers 504 is that spatially local correlation of the input data can exploited by enforcing a local connectivity pattern between nodes of adjacent layers, in particular by each node being connected to only a small region of the nodes of the preceding layer.

In embodiment shown in FIG. 5, the input layer 502 comprises 36 nodes 512, arranged as a two-dimensional 6×6 matrix. The convolutional layer 504 comprises 72 nodes 514, arranged as two two-dimensional 6×6 matrices, each of the two matrices being the result of a convolution of the values of the input layer with a kernel. Equivalently, the nodes 514 of the convolutional layer 504 can be interpreted as arranges as a three-dimensional 6×6×2 matrix, wherein the last dimension is the depth dimension.

A pooling layer 506 can be characterized by the structure and the weights of the incoming edges and the activation function of its nodes 516 forming a pooling operation based on a non-linear pooling function f. For example, in the two dimensional case the values x(n) of the nodes 516 of the pooling layer 506 can be calculated based on the values $x^{(n-1)}$ of the nodes 514 of the preceding layer 504 as $$x^{(n)}[i,j] = f(x^{(n-1)}[id_1, jd_2], \ldots, x^{(n-1)}[id_1+d_1-1, jd_2+d_2-1])$$

In other words, by using a pooling layer 506, the number of nodes 514, 516 can be reduced, by replacing a number $d_1 \cdot d_2$ of neighboring nodes 514 in the preceding layer 504 with a single node 516 being calculated as a function of the values of said number of neighboring nodes in the pooling layer. In particular, the pooling function f can be the max-function, the average or the L2-Norm. In particular, for a pooling layer 506 the weights of the incoming edges are fixed and are not modified by training.

The advantage of using a pooling layer 506 is that the number of nodes 514, 516 and the number of parameters is reduced. This leads to the amount of computation in the network being reduced and to a control of overfitting.

In the embodiment shown in FIG. 5, the pooling layer 506 is a max-pooling, replacing four neighboring nodes with only one node, the value being the maximum of the values of the four neighboring nodes. The max-pooling is applied to each d-dimensional matrix of the previous layer; in this embodiment, the max-pooling is applied to each of the two two-dimensional matrices, reducing the number of nodes from 72 to 18.

A fully-connected layer 508 can be characterized by the fact that a majority, in particular, all edges between nodes 516 of the previous layer 506 and the nodes 518 of the fully-connected layer 508 are present, and wherein the weight of each of the edges can be adjusted individually.

In this embodiment, the nodes 516 of the preceding layer 506 of the fully-connected layer 508 are displayed both as two-dimensional matrices, and additionally as non-related nodes (indicated as a line of nodes, wherein the number of nodes was reduced for a better presentability). In this embodiment, the number of nodes 518 in the fully connected layer 508 is equal to the number of nodes 516 in the preceding layer 506. Alternatively, the number of nodes 516, 518 can differ.

Furthermore, in this embodiment, the values of the nodes 520 of the output layer 510 are determined by applying the Softmax function onto the values of the nodes 518 of the preceding layer 508. By applying the Softmax function, the sum the values of all nodes 520 of the output layer 510 is 1, and all values of all nodes 520 of the output layer are real numbers between 0 and 1.

A convolutional neural network 500 can also comprise a ReLU (rectified linear units) layer or activation layers with non-linear transfer functions. In particular, the number of nodes and the structure of the nodes contained in a ReLU layer is equivalent to the number of nodes and the structure of the nodes contained in the preceding layer. In particular, the value of each node in the ReLU layer is calculated by applying a rectifying function to the value of the corresponding node of the preceding layer.

The input and output of different convolutional neural network blocks can be wired using summation (residual/dense neural networks), element-wise multiplication (attention) or other differentiable operators. Therefore, the convolutional neural network architecture can be nested rather than being sequential if the whole pipeline is differentiable.

In particular, convolutional neural networks 500 can be trained based on the backpropagation algorithm. For preventing overfitting, methods of regularization can be used, e.g. dropout of nodes 512-520, stochastic pooling, use of artificial data, weight decay based on the L1 or the L2 norm, or max norm constraints. Different loss functions can be combined for training the same neural network to reflect the joint training objectives. A subset of the neural network parameters can be excluded from optimization to retain the weights pretrained on another datasets.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIG. 1. Certain steps or functions of the methods and workflows described herein, including one or more of the steps or functions of FIG. 1, may be performed by a server or by another processor in a network-based cloud-computing system. Certain steps or functions of the methods and workflows described herein, including one or more of the steps of FIG. 1, may be performed by a client computer in a network-based cloud computing system. The steps or functions of the methods and workflows described herein, including one or more of the steps of FIG. 1, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIG. 1, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 6:
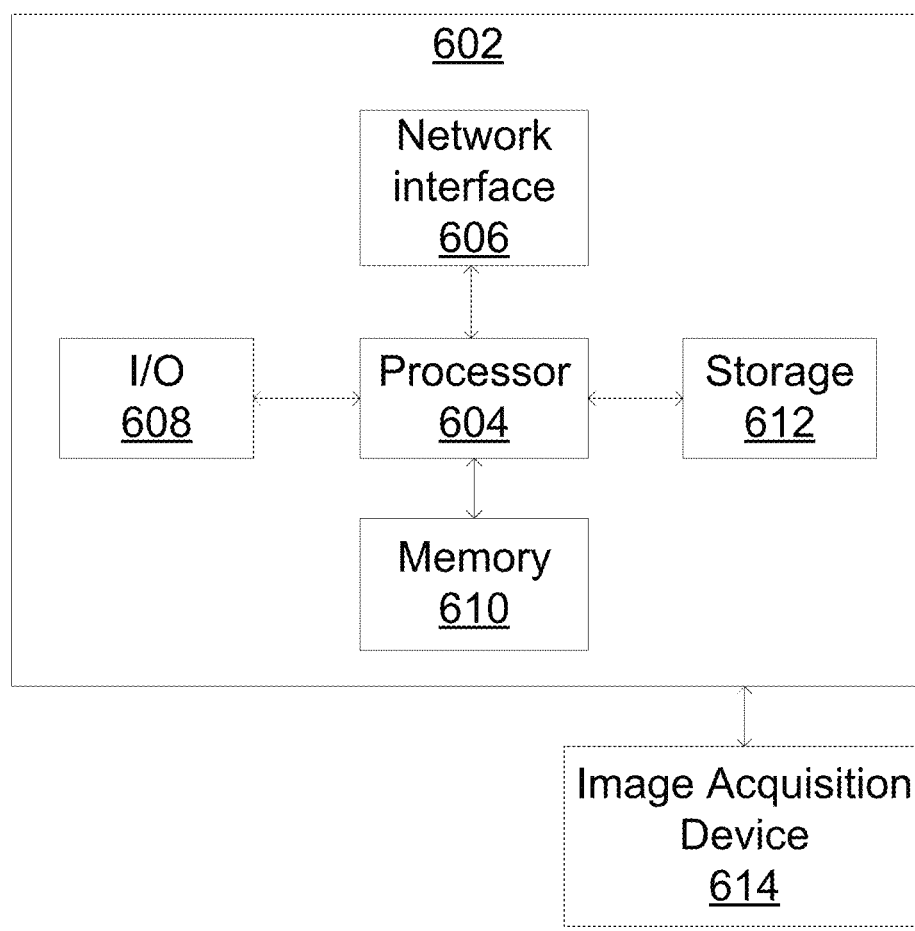
FIG. 6 shows a high-level block diagram of a computer that may be used to implement one or more embodiments.

A high-level block diagram of an example computer 602 that may be used to implement systems, apparatus, and methods described herein is depicted in FIG. 6. Computer 602 includes a processor 604 operatively coupled to a data storage device 612 and a memory 610. Processor 604 controls the overall operation of computer 602 by executing computer program instructions that define such operations. The computer program instructions may be stored in data storage device 612, or other computer readable medium, and loaded into memory 610 when execution of the computer program instructions is desired. Thus, the method and workflow steps or functions of FIG. 1 can be defined by the computer program instructions stored in memory 610 and/or data storage device 612 and controlled by processor 604 executing the computer program instructions. For example, the computer program instructions can be implemented as computer executable code programmed by one skilled in the art to perform the method and workflow steps or functions of FIG. 1. Accordingly, by executing the computer program instructions, the processor 604 executes the method and workflow steps or functions of FIG. 1. Computer 602 may also include one or more network interfaces 606 for communicating with other devices via a network. Computer 602 may also include one or more input/output devices 608 that enable user interaction with computer 602 (e.g., display, keyboard, mouse, speakers, buttons, etc.).

Processor 604 may include both general and special purpose microprocessors, and may be the sole processor or one of multiple processors of computer 602. Processor 604 may include one or more central processing units (CPUs), for example. Processor 604, data storage device 612, and/or memory 610 may include, be supplemented by, or incorporated in, one or more application-specific integrated circuits (ASICs) and/or one or more field programmable gate arrays (FPGAs).

Data storage device 612 and memory 610 each include a tangible non-transitory computer readable storage medium. Data storage device 612, and memory 610, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 608 may include peripherals, such as a printer, scanner, display screen, etc. For example, input/output devices 608 may include a display device such as a cathode ray tube (CRT) or liquid crystal display (LCD) monitor for displaying information to the user, a keyboard, and a pointing device such as a mouse or a trackball by which the user can provide input to computer 602.

An image acquisition device 614 can be connected to the computer 602 to input image data (e.g., medical images) to the computer 602. It is possible to implement the image acquisition device 614 and the computer 602 as one device. It is also possible that the image acquisition device 614 and the computer 602 communicate wirelessly through a network. In a possible embodiment, the computer 602 can be located remotely with respect to the image acquisition device 614.

Any or all of the systems and apparatus discussed herein may be implemented using one or more computers such as computer 602.

One skilled in the art will recognize that an implementation of an actual computer or computer system may have other structures and may contain other components as well, and that FIG. 6 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A computer-implemented method comprising:
receiving one or more input medical images of a vessel of a patient;
defining a lesion in the one or more input medical images;
defining a region of interest around the lesion in the one or more input medical image by:
detecting a centerline of the vessel in the one or more input medical images,
detecting a start marker and an end marker of the lesion along the centerline in the one or more input medical images based on the defining of the lesion, and
defining the region of interest in the one or more input medical images by segmenting a section of the vessel between the start marker and the end marker;
extracting radiomic features from the region of interest, the radiomic features capturing textural patterns of the region of interest;
determining an assessment of the lesion using a machine learning based classifier network based on the radiomic features; and
outputting the assessment of the lesion,
wherein the machine learning based classifier network is constructed by:
extracting one or more radiomic features from a training dataset,
sampling the one or more radiomic features to balance the training dataset,
selecting a feature set from the one or more sampled radiomic features, and
constructing the machine learning based classifier based on the set of features.

2. The computer-implemented method of claim 1, wherein determining an assessment of the lesion using a machine learning based classifier network based on the radiomic features comprises:
classifying the lesion as being vulnerable plaque or non-vulnerable plaque.

3. The computer-implemented method of claim 1, wherein determining an assessment of the lesion using a machine learning based classifier network based on the radiomic features comprises:
determining a probability score indicating a degree of vulnerability of the lesion.

4. The computer-implemented method of claim 1, wherein determining an assessment of the lesion using a machine learning based classifier network based on the radiomic features comprises:
determining a classification of a type of vulnerable plaque of the lesion.

5. The computer-implemented method of claim 1, wherein defining the region of interest in the one or more input medical images by segmenting a section of the vessel between the start marker and the end marker comprises:
automatically defining the region of interest based on at least one of a segmentation of an outer wall of a coronary artery or a segmentation of coronary lumen.

6. The computer-implemented method of claim 5, wherein automatically defining the region of interest based on at least one of a segmentation of an outer wall of a coronary artery or a segmentation of coronary lumen comprises:
automatically defining the region of interest as a segmentation mask of the outer wall of the coronary artery.

7. The computer-implemented method of claim 5, wherein automatically defining the region of interest based on at least one of a segmentation of an outer wall of a coronary artery or a segmentation of coronary lumen comprises:
defining the region of interest as a segmentation mask of the outer wall of a coronary artery excluding the coronary lumen.

8. The computer-implemented method of claim 5, wherein automatically defining the region of interest based on at least one of a segmentation of an outer wall of a coronary artery or a segmentation of coronary lumen comprises:
defining the region of interest as a segmentation mask surrounding the outer wall of the coronary artery.

9. The computer-implemented method of claim 1, wherein the radiomic features comprise one or more of first order statistical features, second order statistical features, or higher order statistical features.

10. The computer-implemented method of claim 1, wherein the radiomic features comprise one or more of size and shape based features, descriptors of an image intensity histogram of the input medical image, descriptors of relationships between image voxels, or fractal features.

11. The computer-implemented method of claim 1, wherein extracting radiomic features from the region of interest comprises:
selecting a best set of the radiomic features for determining the assessment of the lesion.

12. The computer-implemented method of claim 1, further comprising:
receiving an additional input medical image of the lesion, the additional input medical image acquired at a different time point than the input medical image;
repeating the defining, the extracting, and the determining using the additional input medical image as the input medical image to determine an additional assessment of the lesion; and
presenting changes in the assessment of the lesion and the additional assessment of the lesion.

13. The computer-implemented method of claim 1, wherein the input medical image is a computed tomography image of coronary plaque.

14. An apparatus comprising:
 means for receiving one or more input medical images of a vessel of a patient;
 means for defining a lesion in the one or more input medical images;
 means for defining a region of interest around the lesion in the one or more input medical images by:
  detecting a centerline of the vessel in the one or more input medical images,
  detecting a start marker and an end marker of the lesion along the centerline in the one or more input medical images based on the defining of the lesion, and
  defining the region of interest in the one or more input medical images by segmenting a section of the vessel between the start marker and the end marker;
 means for extracting radiomic features from the region of interest, the radiomic features capturing textural patterns of the region of interest;
 means for determining an assessment of the lesion using a machine learning based classifier network based on the radiomic features; and
 means for outputting the assessment of the lesion,
 wherein the machine learning based classifier network is constructed by:
  extracting one or more radiomic features from a training dataset,
  sampling the one or more radiomic features to balance the training dataset,
  selecting a feature set from the one or more sampled radiomic features, and constructing the machine learning based classifier based on the set of features.

15. The apparatus of claim 14, wherein the means for determining an assessment of the lesion using a machine learning based classifier network based on the radiomic features comprises:
 means for classifying the lesion as being vulnerable plaque or non-vulnerable plaque.

16. The apparatus of claim 14, wherein the means for determining an assessment of the lesion using a machine learning based classifier network based on the radiomic features comprises:
 means for determining a probability score indicating a degree of vulnerability of the lesion.

17. The apparatus of claim 14, wherein the means for determining an assessment of the lesion using a machine learning based classifier network based on the radiomic features comprises:
 means for determining a classification of a type of vulnerable plaque of the lesion.

18. The apparatus of claim 14, wherein the means for defining the region of interest in the one or more input medical images by segmenting a section of the vessel between the start marker and the end marker comprises:
 means for automatically defining the region of interest based on at least one of a segmentation of an outer wall of a coronary artery or a segmentation of coronary lumen.

19. The apparatus of claim 18, wherein the means for automatically defining the region of interest based on at least one of a segmentation of an outer wall of a coronary artery or a segmentation of coronary lumen comprises:
 means for automatically defining the region of interest as a segmentation mask of the outer wall of the coronary artery.

20. The apparatus of claim 18, wherein the means for automatically defining the region of interest based on at least one of a segmentation of an outer wall of a coronary artery or a segmentation of coronary lumen comprises:
 means for defining the region of interest as a segmentation mask of the outer wall of a coronary artery excluding the coronary lumen.

21. The apparatus of claim 18, wherein the means for automatically defining the region of interest based on at least one of a segmentation of an outer wall of a coronary artery or a segmentation of coronary lumen comprises:
 means for defining the region of interest as a segmentation mask surrounding the outer wall of the coronary artery.

22. A non-transitory computer readable medium storing computer program instructions, the computer program instructions when executed by a processor cause the processor to perform operations comprising:
 receiving one or more input medical images of a vessel of a patient;
 defining a lesion in the one or more input medical images;
 defining a region of interest around the lesion in the one or more input medical image by:
  detecting a centerline of the vessel in the one or more input medical images,
  detecting a start marker and an end marker of the lesion along the centerline in the one or more input medical images based on the defining of the lesion, and
  defining the region of interest in the one or more input medical images by segmenting a section of the vessel between the start marker and the end marker;
 extracting radiomic features from the region of interest, the radiomic features capturing textural patterns of the region of interest;
 determining an assessment of the lesion using a machine learning based classifier network based on the radiomic features; and
 outputting the assessment of the lesion,
 wherein the machine learning based classifier network is constructed by:
  extracting one or more radiomic features from a training dataset,
  sampling the one or more radiomic features to balance the training dataset,
  selecting a feature set from the one or more sampled radiomic features, and constructing the machine learning based classifier based on the set of features.

23. The non-transitory computer readable medium of claim 22, wherein the radiomic features comprise one or more of first order statistical features, second order statistical features, or higher order statistical features.

24. The non-transitory computer readable medium of claim 22, wherein the radiomic features comprises one or more of size and shape based features, descriptors of an image intensity histogram of the input medical image, descriptors of relationships between image voxels, or fractal features.

25. The non-transitory computer readable medium of claim 22, the operations further comprising:
 receiving an additional input medical image of the lesion, the additional input medical image acquired at a different time point than the input medical image;

repeating the defining, the extracting, and the determining using the additional input medical image as the input medical image to determine an additional assessment of the lesion; and presenting changes in the assessment of the lesion and the additional assessment of the lesion.

\* \* \* \* \*